United States Patent [19]

Ito et al.

[11] Patent Number: 5,708,271
[45] Date of Patent: Jan. 13, 1998

[54] NON-DESTRUCTIVE SUGAR CONTENT MEASURING APPARATUS

[75] Inventors: Masahiro Ito; Junji Iida; Akira Terashima, all of Chiba; Toshiki Kishimoto, Tokyo, all of Japan

[73] Assignee: Sumitomo Metal Mining Co., Ltd., Tokyo, Japan

[21] Appl. No.: 577,542

[22] Filed: Dec. 22, 1995

[30] Foreign Application Priority Data

| Dec. 28, 1994 | [JP] | Japan | 6-327101 |
| Dec. 28, 1994 | [JP] | Japan | 6-327126 |
| Dec. 28, 1994 | [JP] | Japan | 6-327127 |
| Dec. 28, 1994 | [JP] | Japan | 6-327128 |
| Apr. 18, 1995 | [JP] | Japan | 7-116398 |

[51] Int. Cl.$^6$ .................................. G01J 5/02
[52] U.S. Cl. ................... 250/339.11; 250/339.12; 250/910
[58] Field of Search .............. 356/432, 51; 250/910, 250/339.12, 339.11, 341.1, 341.8

[56] References Cited

U.S. PATENT DOCUMENTS 5,089,701 2/1992 Dull et al. .................. 250/339.12

FOREIGN PATENT DOCUMENTS

| 1-216265 | 8/1989 | Japan . |
| 1-235850 | 9/1989 | Japan . |
| 1-301147 | 12/1989 | Japan . |
| 2-147940 | 6/1990 | Japan . |
| 3-48138 | 3/1991 | Japan . |
| 3-176645 | 7/1991 | Japan . |
| 4-104041 | 4/1992 | Japan . |
| 4-208842 | 7/1992 | Japan . |
| 5-34281 | 2/1993 | Japan . |
| 5-34335 | 2/1993 | Japan . |
| 5-172549 | 7/1993 | Japan . |
| 5-288674 | 11/1993 | Japan . |
| 6-15236 | 1/1994 | Japan . |

OTHER PUBLICATIONS

Sumio Kawano et al., "Nondestructive Determination of Sugar Content in Satsuma Mandarin using Near Infrared (NIR) Transmittance", J. Japan. Soc. Hort. Sci. 62(2), pp. 465–470, 1993 (no month available).

Primary Examiner—Frank G. Font
Assistant Examiner—Amanda Merlino
Attorney, Agent, or Firm—Armstrong, Westerman, Hattori, McLeland & Naughton

[57] ABSTRACT

A non-destructive sugar content measuring apparatus for determining the sugar content of a vegetable or fruit by measuring absorption of light in sugar when near infrared light is made incident on the vegetable or fruit; comprising at least one light source that emits light rays having three kinds of wavelengths within a wavelength range of from 860 nm to 960 nm, and a detector that detects the absorption of light. The detector is disposed at a position except the position on an extended line of a straight line that connects i) the center of a light-incident area formed on the surface of the vegetable or fruit by the light emitted from the light source and incident on the vegetable or fruit and ii) the center of the vegetable or fruit, and at the same time at a position where the light-incident area formed on the surface of the vegetable or fruit by the incident light and the detection area formed on the surface of the vegetable or fruit by the light emergent from the vegetable or fruit and to be received by the detector do not overlap each other. This apparatus effectively enables non-destructive measurement of sugar content of vegetables and fruits in an accuracy of about plus-minus 1.0°Brix, which is a resolving limit of sugar content that can be perceived by humans.

15 Claims, 8 Drawing Sheets

NON-DESTRUCTIVE SUGAR CONTENT MEASURING APPARATUS

BACKGROUND OF THE INVENTION

1. Field of the Invention

This invention relates to a non-destructive sugar content measuring apparatus applied to vegetables and fruits, and more particularly relates to a non-destructive sugar content measuring apparatus which is applicable to large vegetables and fruits such as muskmelons and watermelons and can measure their sugar content in a high accuracy.

2. Description of the Related Art

As apparatus for non-destructive measurement of the sugar content of vegetables and fruits, apparatus that determine the sugar content by measuring absorption of light in sugar when infrared light or visible light is made incident on vegetables and fruits are known in the art. Such apparatus are reported in Japanese Patent Applications Laid-open No. 1-301147 and No., 3-176645 as an apparatus that determines the sugar content on the basis of reflected light, and in Journal of The Japanese Society for Horticultural Science, No. 2, Vol. 62, pp.465–470, 1993, as an apparatus that determines the sugar content on the basis of transmitted light.

In the apparatus that determines the sugar content on the basis of reflected light, a light source and a detector are disposed on the same side as viewed from, e.g., a fruit. In the apparatus that determines the sugar content on the basis of transmitted light, the light source and the detector are disposed at opposite positions interposing the fruit between them. In these apparatus, the light is emitted from the light source toward the center of the fruit (since vegetables and fruits are natural products and rarely have a perfectly spherical shape, the "center" is meant to be the center or substantially the center of a fruit). The light emitted from the light source and incident on the fruit forms a light-incident area on the surface of the fruit, and the light emergent from the fruit and to be received by the detector forms a detection area on the surface of the fruit, where an axis (a straight line) that connects the center of the light-incident area and the center of the fruit and an axis (a straight line) that connects the center of detection area and the center of the fruit make an angle (herein called "disposition angle") of 0 degree in the case of the apparatus that determines the sugar content on the basis of reflected light and an angle of 180 degrees in the case of the apparatus that determines the sugar content on the basis of transmitted light. Hitherto, the measurement has not been made at disposition angles other than these angles as having been considered useless.

Now, the light incident on the fruit scatters and is absorbed inside the fruit, and becomes emergent from the fruit. Hence, in respect of the information on sugar in the fruit, there is no substantial difference between the light commonly regarded as transmitted light whose incident direction and detection direction are in agreement and the light regarded as reflected light whose incident direction and detection direction are just reverse, and what is different is only the direction of emergence of the light.

When, however, the disposition angle is set at 0 degree, the light reflected in the vicinity of the surface of the fruit (which includes light reflected on the surface of the fruit and light having entered into the fruit but reflected at the rind) is contained in a large proportion in the light to be detected by the detector (i.e., detection light), and hence, though having the detection light itself in a large amount, has the information on sugar in sarcocarp in a small proportion. Thus, in order to detect the sugar content in an accuracy of about plus-minus 1.0°Brix, which is a resolving limit of sugar content that can be perceived by humans, the amount of detection light must be read at greater figures, where a problem may arise (here, the accuracy required is plus-minus 1.0°Brix as an error between an actual sugar content determined by destructive examination using a refraction saccharometer and a sugar content determined by non-destructive measurement of sugar content.). Especially in the case of fruits having a thick outer covering such as muskmelons and watermelons, the amount of information relating to the sugar, contained in the detection light, is so much smaller that it becomes necessary to read the amount of detection light in a precision of six figures or more. Usually, the amount of light is read in a precision of about four figures and no sugar content can be detected in a sufficient accuracy when the disposition angle is 0 degree. If it is attempted to improve the accuracy in the detection of sugar content at a disposition angle of 0 degree, the data can not help being sampled for a prolonged time, bringing about the problem that such a method can not be used when a large number of muskmelons or the like are sorted by sugar content.

On the other hand, in the case when the disposition angle is set at 180 degrees, the light having the information relating to sugar is contained in the detection light in a large proportion, and hence the amount of detection light may be read at a precision of about two figures. Since, however, the incident light having entered into a fruit increasingly attenuates in accordance with the distance at which the light transmits inside the fruit, the intensity of the light reaching the detector decreases with an increase in size of the vegetables and fruits to be measured, bringing about the problem that the detection itself is not easy. For example, in some melons, when laser light with a wavelength of 930 nm and an output of 100 mW is made incident on melons, the light transmitting the melons and reaching the detector attenuates to an amount of 10 pW, i.e., by as many as ten figures. In order to detect the sugar content in an accuracy of about plus-minus 1.0°Brix, the detection must be made in an amount of light of about 10 nW on account of the problem of noise light, even if a detector with a high sensitivity is used. In the case of the apparatus having the disposition angle of 180 degrees, it is difficult to detect the sugar content in an accuracy of about plus-minus 1.0°Brix. Incidentally, the amount of detection light can be increased to 10 nW by setting the amount of incident light at 10 W, but, on the other hand, the surfaces of melons may burn by the action of the incident light to cause a difficulty in the non-destructive examination.

SUMMARY OF THE INVENTION

Accordingly, an object of the present invention is to provide a non-destructive sugar content measuring apparatus that enables non-destructive measurement of sugar content of vegetables and fruits in an accuracy of about plus-minus 1.0°Brix, which is a resolving limit of sugar content that can be perceived by humans, without regard to the size of the vegetables and fruits and without need to read the amount of detection light at greater figures.

Another object of the present invention is to provide a non-destructive sugar content measuring apparatus that can measure the sugar content at a coefficient of correlation of not less than 0.9 between an actual sugar content determined by destructive examination and a sugar content determined on the basis of light, without regard to the size of the vegetables and fruits and without need to read the amount of detection light at greater figures.

The present invention provides a non-destructive sugar content measuring apparatus for determining the sugar content of a vegetable or fruit by measuring absorption of light in sugar when near infrared light is made incident on the vegetable or fruit; said apparatus comprising; at least one light source that emits light rays having three kinds of wavelengths within a wavelength range of from 860 nm to 960 nm, and a detector that detects the absorption of light; the detector being disposed at a position except the position on an extended line of a straight line that connects i) the center of a light-incident area formed on the surface of the vegetable or fruit by the light emitted from the light source and incident on the vegetable or fruit and ii) the center of the vegetable or fruit, and at the same time at a position where the light-incident area formed on the surface of the vegetable or fruit by the incident light and the detection area formed on the surface of the vegetable or fruit by the light emergent from the vegetable or fruit and to be received by the detector do not overlap each other.

DESCRIPTION OF THE PREFERRED EMBODIMENTS

Under the technical background as previously discussed, the present inventors made extensive studies in order to bring out a non-destructive sugar content measuring apparatus that enables non-destructive examination of sugar content of vegetables and fruits in an accuracy of about plus-minus 1.0°Brix, which is a resolving limit of sugar content that can be perceived by humans. As a result, they have reached a technical discovery as stated below.

That is, they have found that, when light is emitted from a light source and incident on, e.g., a fruit such as a muskmelon, toward its center (in this case, the light thus emitted is incident on the fruit in the direction substantially perpendicular to its surface), the light incident on and having entered into the fruit is not only emergent from the fruit on the side of the light source and on the side opposite thereto, but also similarly emergent from anywhere on the periphery of the fruit, provided that the intensity of light and the amount of information on sugar, contained in the light, are different depending on places. Under such situation, they have confirmed that the light emergent from the fruit can be detected also when, or rather can be detected in a higher accuracy when, the detector is not disposed at the disposition angle of 0 degree or 180 degrees having been hitherto so set. Thus, they have found that the amount of detection light can be well ensured without being affected by the light reflected in the vicinity of the surface of the fruit and even with use of a light source having an intensity that does not cause the surface of the fruit to burn, when the detector is disposed at a proper angle other than the disposition angles conventionally set.

They have also confirmed that the light to be made incident on the surface of the fruit need not be emitted in the direction toward the center of the fruit (in this case, the light emitted from the light source is incident on the fruit from an oblique direction with respect to its surface).

The non-destructive sugar content measuring apparatus of the present invention accomplished on the basis of such technical discovery has at least one light source that emits light rays having three kinds of wavelengths within a wavelength range of from 860 nm to 960 nm, and a detector that detects the absorption of light, and is characterized in that the detector is disposed at a position except the position on an extended line of a straight line that connects i) the center of a light-incident area formed on the surface of the vegetable or fruit by the light emitted from the light source and incident on the vegetable or fruit and ii) the center of the vegetable or fruit, and at the same time at a position where the light-incident area formed on the surface of the vegetable or fruit by the incident light and the detection area formed on the surface of the vegetable or fruit by the light emergent from the vegetable or fruit and to be received by the detector do not overlap each other.

The present invention will be described below in detail properly with reference to the accompanying drawings.

First of all, in the non-destructive sugar content measuring apparatus according to the present invention, the position on an extended line of a straight line that connects i) the center of a light-incident area formed on the surface of the vegetable or fruit by the light emitted from the light source and incident on the vegetable or fruit and ii) the center of the vegetable or fruit is excluded from the position at which the detector is disposed. Hence, different from the conventional apparatus that determines the sugar content on the basis of transmitted light (having a disposition angle of 180 degrees), it is unnecessary to detect the emergent light having too much transmitted through the sarcocarp of, e.g., a fruit and having attenuated at a high rate. Thus, emergent light having transmitted through the sarcocarp of the fruit over a necessary and sufficient distance and having attenuated at a low rate can be selected as the light to be detected, and hence the amount of detection light can be well ensured without use of a light source having a high output.

The detector is also disposed at the position excluding the above position and at the same time at a position where the light-incident area formed on the surface of the vegetable or fruit by the incident light and the detection area formed on the surface of the vegetable or fruit by the light emergent from the vegetable or fruit and to be received by the detector do not overlap each other. Accordingly, the detector is no longer affected by the light reflected in the vicinity of the surface of the vegetable or fruit, and hence it becomes possible to measure the sugar content of vegetables and fruits in an accuracy of about plus-minus 1.0°Brix, which is a resolving limit of sugar content that can be perceived by humans.

Thus, it becomes possible to make non-destructive measurement of the sugar content of vegetables and fruits in an accuracy of about plus-minus 1.0°Brix, which is a resolving limit of sugar content that can be perceived by humans, without regard to the size of the vegetables and fruits and without need to read the amount of detection light at greater figures.

In the non-destructive sugar content measuring apparatus according to the present invention, the absorption of near infrared light in sugar is measured to determine the sugar content. Sugar has absorption peaks around wavelengths of 910 nm, 1.05 µm and 1.3 µm. The longer the wavelength is, the more greatly the absorption is affected by water. Accordingly, in the non-destructive sugar content measuring apparatus according to the present invention, the absorption peak at 910 nm is utilized, as being less affected by the absorption of light in water, and hence at least one light source that emits light rays with wavelengths ranging from 860 nm to 960 nm is used.

In this non-destructive sugar content measuring apparatus, the sugar content is determined using light rays having three kinds of wavelengths. One of the three wavelengths is set within the range of from 900 nm to 920 nm (second-light wavelength range), which are the absorption wavelengths assigned to the sugar. As for other two wavelengths, they are selected from wavelengths of from 860 nm to 890 nm (first-light wavelength range) and wavelengths of from 920 nm to 960 nm (third-light wavelength range, provided that 920 nm is excluded), which have nothing to do with the light absorption in sugar. Since the light with wavelengths selected in this way is used, the effect of backgrounds having a wavelength dependence can be accurately removed from the absorption of the light having the above wavelengths of from 900 nm to 920 nm, so that the sugar content can be accurately determined. More specifically, the sugar content of vegetables and fruits can be determined at a coefficient of the correlation with an actual sugar content, of not less than 0.9, i.e., in an accuracy of plus-minus 1.0°Brix.

When the light rays having the wavelengths to be used are selected from the group of light rays having the wavelengths within the above wavelength ranges, some combinations of wavelengths thus selected may provide instances in which the resulting value of coefficient of correlation is more than 0.9 as will become clear from the data given in Examples described later.

Such light may preferably be composed of a first light ray having a wavelength ranging between 860 nm and 890 nm, a second light ray having a wavelength ranging between 900 nm and 905 nm or between 910 nm and 915 nm, and a third light ray having a wavelength ranging between more than 920 nm and not more than 925 nm, where a coefficient of correlation of 0.95 or more can be obtained.

It may also be composed of a first light ray having a wavelength ranging between 860 nm and 890 nm, a second light ray having a wavelength ranging between more than 905 nm and not more than 910 nm and a third light ray having a wavelength ranging between more than 920 nm and not more than 925 nm, where a coefficient of correlation of from 0.92 to 0.94 can be obtained.

It may also be composed of a first light ray having a wavelength ranging between 860 nm and 890 nm, a second light ray having a wavelength ranging between 900 nm and 920 nm and a third light ray having a wavelength ranging between more than 925 nm and not more than 930 nm, where a coefficient of correlation of from 0.92 to 0.94 can be obtained.

It may still also be composed of a first light ray having a wavelength ranging between 860 nm and 890 nm, a second light ray having a wavelength ranging between 900 nm and 920 nm and a third light ray having a wavelength ranging between more than 935 nm and not more than 940 nm, where a coefficient of correlation of from 0.92 to 0.94 can be obtained.

As a means for emitting the light rays having these three kinds of wavelengths, it is usually composed of three light sources, or may be composed of a single light source in some cases. As types of the light source, it may include lasers such as a semiconductor laser and a solid-state laser, light-emitting diodes, and halogen lamps, which are appropriately selected in accordance with the types of vegetables and fruits to be measured.

Figure 4A:
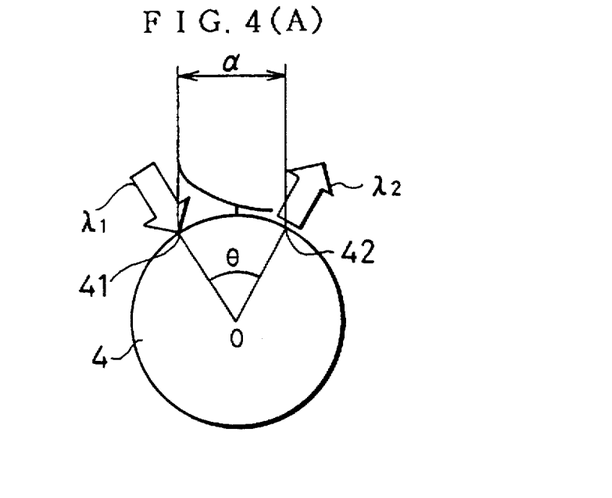
FIGS. 4A, 4B and 4C each illustrate the relationship between the light incident on a fruit (a muskmelon) and the light emergent from the fruit.
Figure 4B:
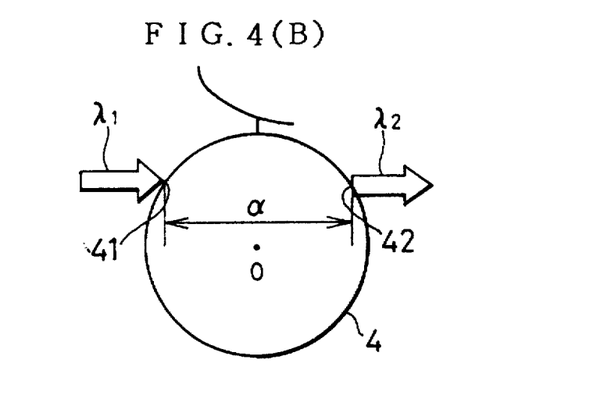
Figure 4C:
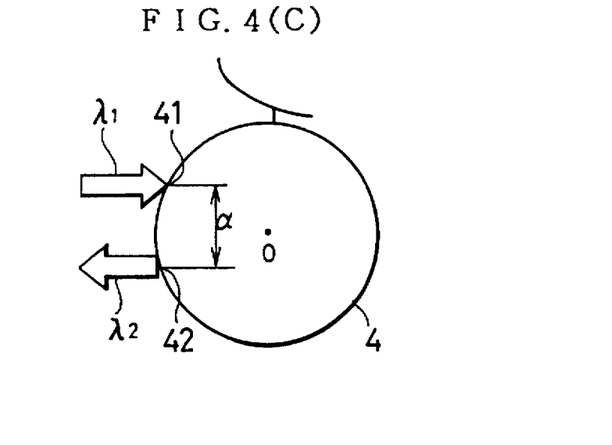

The incident direction of the light emitted from the light source and incident on the vegetable or fruit and the specific position at which the detector for detecting the light emergent from the vegetable or fruit will be described below. As shown in FIG. 4A, the light may be emitted from the light source (not shown) toward the center, denoted as O, of a fruit 4 (a muskmelon), and the detector may be disposed at any position except the position on an extended line of a straight line that connects i) the center O of a light-incident area 41 formed on the surface of the fruit 4 by incident light λ1 which is incident on the fruit 4 and ii) the center O of the fruit 4, and at the same time at any position where the light-incident area 41 formed on the surface of the fruit 4 by the incident light λ1 and a detection area 42 formed on the surface of the fruit by emergent light λ2 which is emergent from the fruit 4 and to be received by the detector (not shown) do not overlap each other. Alternatively, as shown in FIGS. 4B and 4C, the light may be emitted in the direction kept aside from the center O of the fruit 4 (i.e., the incident direction of the light incident on the surface of the fruit is set in the direction not falling in agreement with the direction extended from a straight line connecting the center of the light-incident area on the surface of the fruit and the center of the fruit), and the detector may be disposed at any position except the position on an extended line of a straight line that connects i) the center O of a light-incident area 41 formed on the surface of the fruit 4 by incident light λ1 which is incident on the fruit 4 and ii) the center O of the fruit 4, and at the same time at any position where the light-incident area 41 formed on the surface of the fruit 4 by the incident light λ1 and a detection area 42 formed on the surface of the fruit 4 by emergent light λ2 which is emergent from the fruit 4 and to be received by the detector (not shown) do not overlap each other.

Figure 5:
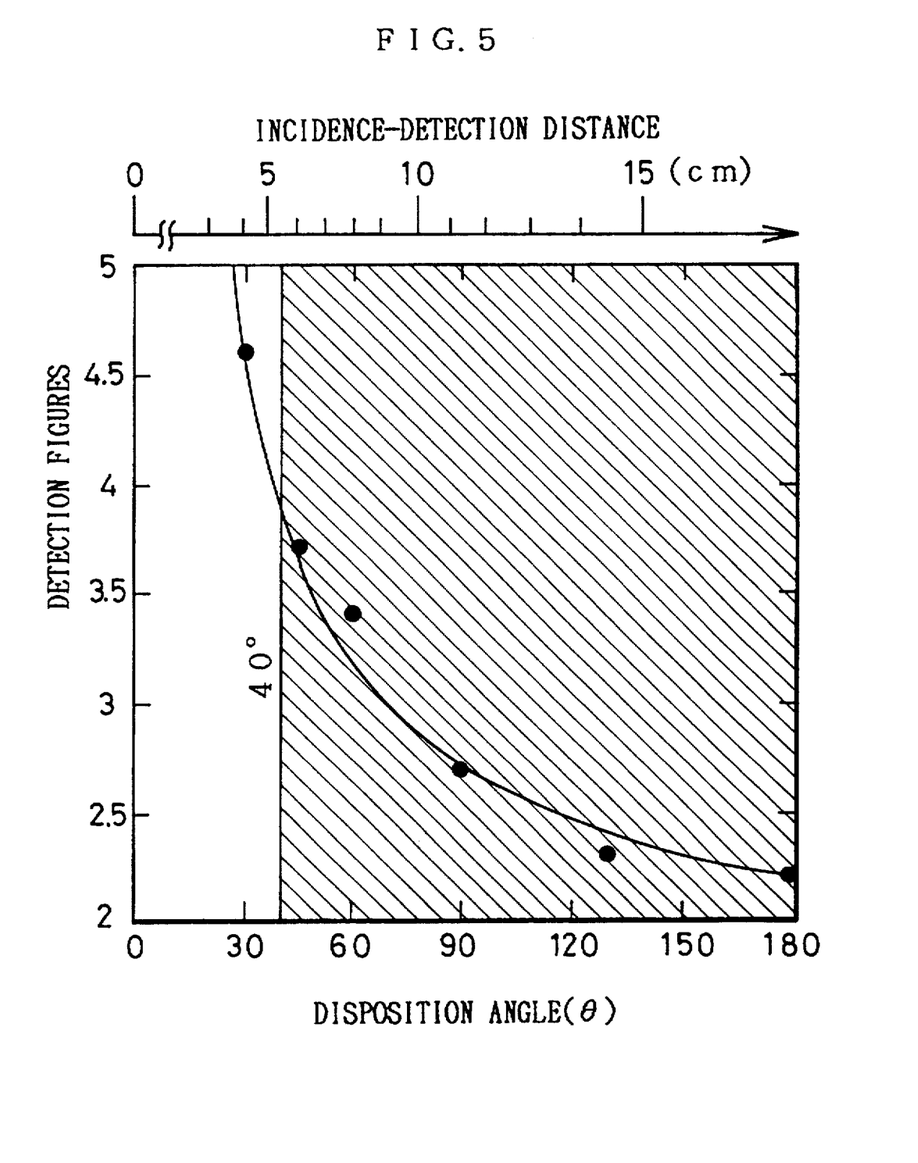
FIG. 5 is a graph showing the dependence of detection figures (figures at which the amount of detection light is read) on disposition angles, and the dependence of the detection figures on the distance between the center of light-incident area and the center of detection area (in the drawing "incidence-detection distance").

Now, how the disposition angle (θ) participates in the measurement when the light is emitted from the light source toward the center O of the fruit 4 will be studied. Studies will be first made on the dependence on disposition angles, of detection figures (figures at which the amount of detection light is read) in the detection of the amount of light necessary for measuring the sugar content in an accuracy of plus-minus 1.0°Brix or higher (i.e., an error between an actual sugar content determined by destructive examination using a refraction saccharometer and a sugar content determined by non-destructive measurement of sugar content is plus-minus 1.0°Brix or below). FIG. 5 shows the dependence of the detection figures on the disposition angle in respect of a muskmelon of about 16 cm diameter. There are seen the tendencies that detection figures decrease with an increase in the disposition angle and the detection figures saturate at a disposition angle of 130 degrees or greater. As previously stated, the detection figures are about four in usual detectors, and hence the disposition angle (θ) must be set at 40 degrees or greater in order to detect the sugar content in an accuracy of plus-minus 1.0°Brix or higher.

Figure 6:
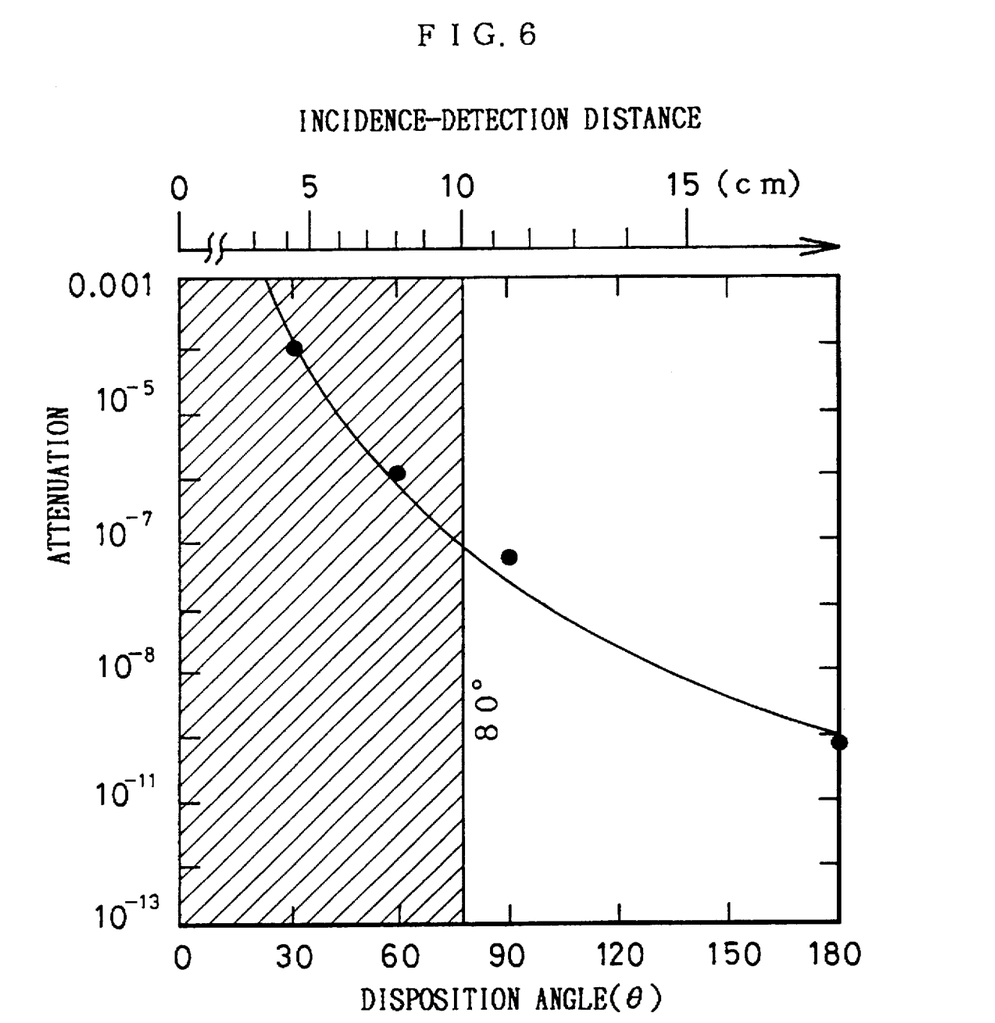
FIG. 6 is a graph showing the dependence of detection figures (figures at which the amount of detection light is read) on disposition angles, and the dependence of attenuation of detection light intensity on the distance between the center of light-incident area and the center of detection area.

Next, studies will be made on the dependence of attenuation of detection light intensity on the disposition angles. FIG. 6 shows the dependence of the attenuation of detection light intensity on the disposition angles in an instance where light of 930 nm, which is near to a peak wavelength 910 nm in the absorption ascribable to sugar and not affected by the absorption ascribable to sugar, is made incident on a muskmelon of about 16 cm diameter. The attenuation is minimum when the disposition angle is 0 degree, and increases with an increase in the disposition angle to reach a maximum at an disposition angle (θ) of 180 degrees. Namely, the detection light intensity (the amount of detection light) decreases with an increase in the disposition angle (θ), and in some cases attenuates by as many as ten figures at the disposition angle (θ) of 180 degrees, which is variable depending on individual muskmelons. In this case, among the light rays having the three kinds of wavelengths as used in the present invention, the light subject to attenuation is the third light, having a long wavelength and capable of transmitting through the muskmelon with difficulty. Meanwhile, a laser diode having an oscillation wavelength around 930 nm, which emits the third light, has an output of about 100 mW in usual cases. Hence, in order to measure the sugar content in an accuracy of plus-minus 1.0°Brix or higher, the disposition angle must be set at an angle where the attenuation becomes greater than $1 \times 10^{-7}$, i.e., the disposition angle (θ) must be set at 80 degrees or smaller so that the amount or intensity of detection light can be 10 nW or more. Accordingly, in order to measure the sugar content in an accuracy of plus-minus 1.0°Brix or higher, the disposition angle (θ) in the case when the light is emitted from the light source toward the center O of the fruit 4 as shown in FIG. 4A must be controlled within the range of from 40 degrees to 80 degrees when the fruit is a muskmelon.

These studies on the disposition angle (θ) can also be replaced by the linear distance (α) corresponding to a straight line that connects the center of the light-incident area 41 formed on the surface of the fruit 4 by incident light λ1 and the center of the detection area 42. That is, FIG. 5 is also a graph showing the dependence of the detection figures on the distance between the center of light-incident area and the center of detection area. FIG. 6 is also a graph showing the dependence of attenuation of detection light intensity on the distance between the center of light-incident area and the center of detection area. As is seen from the data in FIG. 5, in order to detect the sugar content in an accuracy of plus-minus 1.0°Brix or higher, the distance (α) between the centers of the light-incident and detection areas must be controlled to be about 5 cm or more. Also, as will be seen from the data in FIG. 6, in order to detect the sugar content in an accuracy of plus-minus 1.0°Brix or higher, conditions under which the attenuation becomes greater than $1 \times 10^{-7}$, i.e., the distance (α) between the centers of the light-incident and detection areas must be controlled to be 10 cm or less so that the amount or intensity of detection light can be 10 nW or more. Here, note that these data are values determined on the muskmelon of about 16 cm diameter. Also, muskmelons usually have diameters of 16±4 cm. As their diameters become smaller than 16 cm, the distance (α) between the centers of the light-incident and detection areas becomes smaller than 5 cm, and its lower limit value is about 4 cm. As their diameters become larger than 16 cm, the distance (α) between the centers of the light-incident and detection areas becomes larger than 10 cm, and its upper limit value is about 13 cm. Accordingly, in order to measure the sugar content in an accuracy of plus-minus 1.0°Brix or higher, the distance (α) between the centers of the light-incident and detection areas in the case when the light is emitted from the light source toward the center O of the fruit 4 as shown in FIG. 4A must be controlled within the range of from 4 cm to 13 cm in accordance with the above data of analyses.

The conditions concerning the muskmelons in respect of the distance (α) between the centers of the light-incident and detection areas are also established when the light is emitted in the direction kept aside from the center O of the fruit 4 (a muskmelon) as shown in FIGS. 4B and 4C. When the light is made incident on the fruit under conditions as shown in FIGS. 4B and 4C, in order to measure the sugar content in an accuracy of plus-minus 1.0°Brix or higher, the distance (α) must be controlled within the range of from 4 cm to 13 cm. With regard to watermelons, which are larger than the muskmelons, in order to measure the sugar content in an accuracy of plus-minus 1.0°Brix or higher, the distance (α) between the centers of the light-incident and detection areas must be controlled within the range of from 4 cm to 12 cm in accordance with the data which will be given in Examples described later.

In the case when the sugar content is measured on a muskmelon, the values obtained on the sugar content may differ depending on places where the light is made incident (i.e., light-incident positions) on the surface of the muskmelon, resulting in a little lower accuracy of measurement than the accuracy of plus-minus 1.0°Brix, which is a resolving limit of sugar content that can be perceived by humans.

Such differences in the values of sugar content which occur depending on the light-incident positions are presumed to be caused by the presence of nets on the surfaces of muskmelons. More specifically, in the method that determines the sugar content on the basis of light absorption, light rays with a plurality of wavelengths are made incident on a muskmelon, and the amount of light absorbed in sugar is determined from differences in transmittance (or reflectance) occurring when the light with different wavelengths transmits through the sarcocarp of the muskmelon, to determine its sugar content. Accordingly, in order to accurately determine such differences in transmittance (or reflectance), the effect of the surface of the muskmelon upon the incident light must be equal to the respective light rays having different wavelengths. Also, in order to measure the sugar content always under the same conditions, the proportion of the light entering into the muskmelon to the amount of incident light must be equal without regard to the light-incident position.

Since, however, the nets of muskmelons have rough surfaces, the reflectance and diffusion coefficient of the light are considered to greatly differ between the net and the portions other than the net. Hence, when the light is incident on a muskmelon having the net on its surface, the effect of the surface of the muskmelon upon the incident light differs depending on whether or not the net is included in the extent of surface where the light is made incident (i.e., the light-incident area).

Accordingly, the effect of the surface of the muskmelon upon the incident light may preferably be made equal without regard to the position at which the light is made incident. In order to make equal the proportion of the light entering into the muskmelon to the amount of incident light even when the position at which the light is made incident is changed, the proportion held by the net in the extent of the light-incident area may be controlled so as not to change depending on the light-incident position. For this purpose, the extent of the light-incident area may preferably be controlled to be 1 $cm^2$ or more. As an upper limit, the extent of the light-incident area may preferably be controlled to be 20 $cm^2$ or less, because, although the reason is unclear, the values obtained on the sugar content may differ depending on the light-incident positions, if the light-incident area is too large.

In order to make equal the effect of the surface of the muskmelon upon the incident light rays having different wavelengths, the light rays having different wavelengths must have equal extent of the light-incident area on the surface of the muskmelon and also equal light intensity distribution of the light ray incident in the light-incident area. For this purpose, it is effective to make the light incident on the muskmelon after the light rays with different wavelengths, emitted from the light source, have been passed through a diffuser panel. Even when light rays emitted from different light sources have different light intensity distributions, the light rays having been passed through the diffuser panel are diffused in various directions and hence can be converted into incident light rays having equal light intensity distribution. Also, even when light rays are emitted from different light sources, they may be passed through a diffuser panel having the same size, whereby the light can be converted into a beam with a size equal to the size of the diffuser panel, and hence the light rays can be made to have equal extent of the light-incident area.

When the sugar content is measured on fruits of the gourd family such as muskmelons and watermelons and the light is incident on their thick rinds, the light absorbs and scatters at the rind in a large amount to enable no proper measurement. Also, the detection light may become weak to cause a lowering of measurement accuracy. This is because firm and fibrous components are contained in a large quantity in the rind.

The fruits such as muskmelons and watermelons also have thinner rinds in the vicinity of their style portions than in the vicinity of their pedicel portions or in the vicinity of their equatorial portions. However, they have partly thick rinds at the hilum portion at the center of the style portion. For example, in the case of muskmelons from Hokkaido (Japan), they have rinds of 5 mm or more thick in the vicinity of the pedicel portion or in the vicinity of the equatorial portion, and of nearly 10 mm thick in the vicinity of the pedicel portion. On the other hand, they have rinds of less than 5 mm thick in the vicinity of the style portion except the central hilum portion.

Accordingly, the sugar content can be properly and more accurately measured when the light is made incident and detected in the vicinity of the style portion. Incidentally, with regard to the height of the fruit as viewed with its pedicel portion up, its range smaller than 1/50 of the overall height corresponds to the region belonging to the above hilum portion at the center of the style portion, and its range exceeding 1/3 of the overall height corresponds to the region in the vicinity of the pedicel portion or in the vicinity of the equatorial portion where the rind is thick. Hence, in the case when the sugar content is measured on the fruits of the gourd family such as muskmelons and watermelons, the light-incident area formed on the surface of the fruit by the incident light and/or the detection area formed on the surface of the fruit by the light emergent from the fruit and to be received by the detector may preferably be set at a position within the range of from 1/50 to 1/3 of the overall height of the fruit as viewed with its pedicel portion up.

Figure 3:
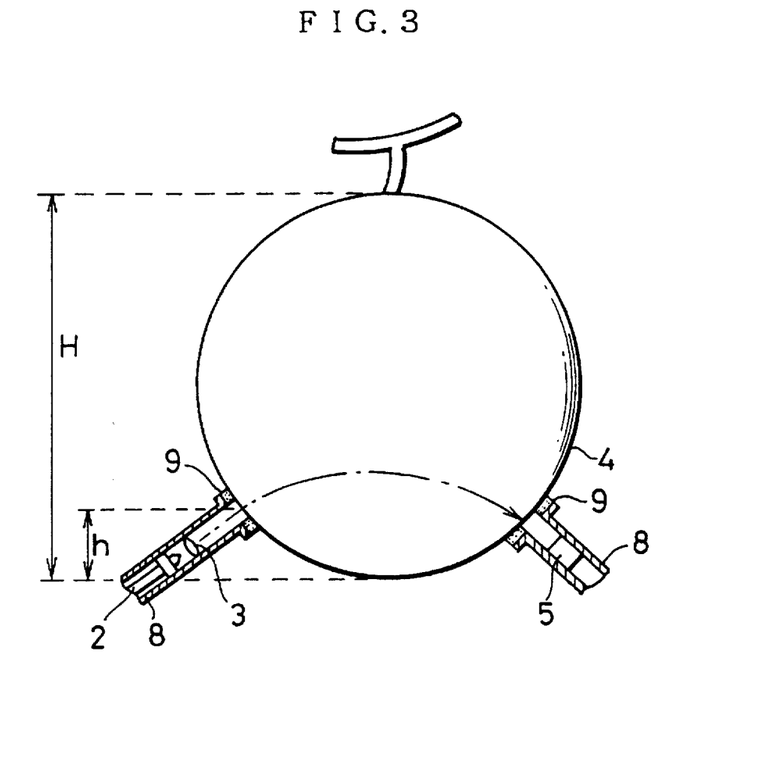
FIG. 3 illustrates the main part to show another embodiment of the present invention.

When both the light-incident area and the detection area are set in the vicinity of the style portion, the direction of light incidence and the direction of detection make a certain angle, and hence in some cases the detector, which is positioned with respect to a light-incidence means such as an optical fiber, does not completely enter into the shade of the object for measurement. In such a case, a noise due to the light not passing through the inside of the fruit and directly or indirectly reaching the detector may come into question. As a countermeasure therefor, a partition (a shielding plate) may be provided between the light-incidence means and the detector. Alternatively, as shown in FIG. 3, the light-incidence means such as an optical fiber 2, or the detector 5 may be held into a tube 8 and also a ring-shaped rubber 9 may be provided at the end of each tube 8 so as to be pressed against a fruit 4 which is the object for measurement. Such a measure is effective as the countermeasure for removing the noise.

Herein, the "pedicel portion" of the fruit refers to the region of fruit where the fruit and its stem are connected or had been connected, and is positioned in symmetry to the hilum-like "style portion" formed of an inflected ovary tip. The "overall height" corresponds to the diameter in the direction of the north to the south, assuming that the center of the "pedicel portion" is regarded as the north and the center of the "style portion" as the south. The "height of the fruit as viewed with its pedicel portion up" corresponds to the ratio to the "overall height", of the distance between the center of the "style portion" and a plane imaginary at an arbitrary point on the surface of the fruit and perpendicular to the north to south axis, passing through that point. Therefore, it follows that "the range of from 1/50 to 1/3 of the overall height of the fruit as viewed with its pedicel portion up" indicates a region of approximately from 19.5 degrees to 73.7 degrees of south latitude (Lat. 19.5°–73.7°S).

In the present invention, there are no particular limitations on methods for making the light incident, for detecting the emergent light, and for calculating the sugar content, and also on the standard of sugar content. The object for measurement and the light-incidence means or the detector may be fixed in a relative fashion, or either may be moved. The light may be incident on one point of the surface, or may be incident on points while scanning. At the time of measurement, the vegetable or fruit may be placed in any manner. It may be placed with its top upwards, downwards, sideways or in any other directions. It may also be put to measurement while being rolled. Also, the vegetable or fruit whose sugar content is measured using the non-destructive sugar content measuring apparatus according to the present invention may include any vegetables and fruits. When measured on relatively small fruits such as apples and peaches, the sugar content can be measured in a higher accuracy than conventional cases. Also when measured on relatively large vegetables and fruits such as muskmelons, watermelons and pumpkins, the sugar content can be measured in a higher accuracy.

As described above, the non-destructive sugar content measuring apparatus according to the present invention have the advantage that it enables non-destructive measurement of sugar content of vegetables and fruits in an accuracy of about plus-minus 1.0°Brix, which is a resolving limit of sugar content that can be perceived by humans, without regard to the size of the vegetables and fruits and without need to read the amount of detection light at greater figures.

Especially when the vegetables and fruits are muskmelons and the detector is so disposed that its disposition angle is 40 degrees to 80 degrees or the detector is so disposed that the linear distance corresponding to a straight line connecting the center of the light-incident area formed on the surface of the fruit by the incident light and the center of the detection area formed on the surface of the fruit by the emergent light is 4 cm to 13 cm, the present apparatus enables non-destructive measurement of sugar content of the muskmelons in an accuracy of plus-minus 1.0°Brix (which is a resolving limit of sugar content that can be perceived by humans) or higher, without need to read the amount of detection light at greater figures.

Similarly, when the vegetables and fruits are watermelons and the detector is so disposed that the linear distance corresponding to a straight line connecting the center of the light-incident area formed on the surface of the fruit by the incident light and the center of the detection area formed on the surface of the fruit by the emergent light is 4 cm to 12 cm, the present apparatus enables non-destructive measurement of sugar content of the muskmelons in an accuracy of plus-minus 1.0°Brix (which is a resolving limit of sugar content that can be perceived by humans) or higher, without need to read the amount of detection light at greater figures.

The present invention will be described below in greater detail by giving Examples and Comparative Examples, also with reference to the drawings.

EXAMPLE 1

Figure 1:
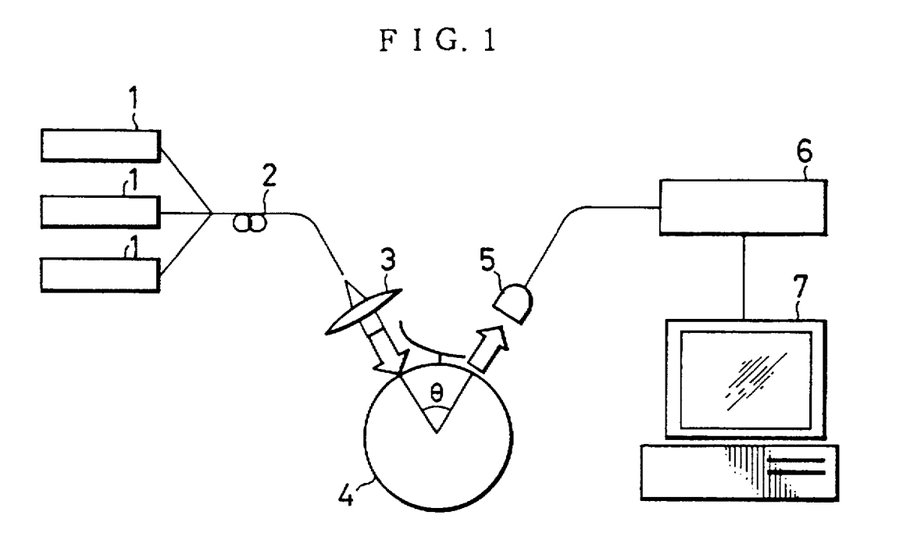
FIG. 1 illustrates the constitution of the non-destructive sugar content measuring apparatus according to an embodiment of the present invention.

Non-destructive measurement of sugar content, using the non-destructive sugar content measuring apparatus according to an embodiment of the present invention will be described with reference to FIG. 1. FIG. 1 illustrates an example of the constitution of the non-destructive sugar content measuring apparatus according to the present invention. As light sources 1, three laser diodes are used, each having a laser output of 100 mW and respectively having oscillation wavelengths of 880 nm, 910 nm and 930 nm. The light rays emitted from the laser diodes are led through an optical fiber 2 and transmitted to a lens 3. After the light rays are formed into parallel rays of light with a beam diameter of 2 cm, the light is incident on a vegetable or fruit (a muskmelon of about 16 cm diameter) 4. The light incident on the vegetable or fruit (hereinafter "muskmelon") 4 is emergent from the muskmelon 4 in every direction on account of the reflection from the surface and the scattering inside the muskmelon 4.

In FIG. 1, the detector 5 is illustrated as if it is formed of a single detecting element. In actual use, it is formed of a plurality of detecting elements in combination so that the detection light emergent from the detection area of the muskmelon 4 can be entirely received by the detector 5 to enhance the detection accuracy. It, however, is optional to constitute the detector with a plurality of detecting elements or a single detecting element.

In the present Example, the light emergent in every direction was detected by means of a detector 5 so positioned as to be in a disposition angle ($\theta$) of 30 degrees, 40 degrees, 60 degrees, 80 degrees, 90 degrees or 180 degrees, to make measurement of the sugar content on 80 muskmelons.

The values of the amount of detection light detected by the detector 5 are converted to digital signals through a 16 bit AD convertor 6 so as to be read in a precision of four figures, and then inputted to a computer 7.

The above muskmelon 4, the optical fiber 2, the detector and so forth are disposed inside a dark room. The sugar content is measured in the dark room. To measure the sugar content, a value of the amount of incident light is beforehand measured and, using this value, a value of the amount of detection light is converted into transmittance (=amount of detection light/amount of incident light). Thereafter the sugar content is calculated according to the following expression (1).

$$Y = AX_1 + BX_2 + CX_3 + D \tag{1}$$

wherein Y is a sugar content (Brix); $X_1$, $X_2$, $X_3$ are each a natural logarithm value of the transmittance of a mushmelon to the light having wavelengths of 880 nm, 910 nm and 930 nm, i.e., an absorption; and A, B, C and D are each a constant determined by minimum involution with use of actual measurements of sugar content determined by a refraction saccharometer (destructive measurement), where A is $-27.39$, B is $68.50$, C is $-41.12$ and D is $12.92$.

At the six kinds of disposition angles (degrees), the non-destructive measurement of sugar content was made on 80 muskmelons to reveal that the coefficient of correlation between the sugar content determined by light-absorption measurement and the actual measurements of sugar content determined by the refraction saccharometer and the errors of measurements of sugar content (Brix) between them were as shown in Table 1 below.

TABLE 1

| Disposition angle ($\theta$) (degrees) | Coefficient of correlation | Errors of measurements of sugar content (Brix) |
|---|---|---|
| 30 | 0.70 | ±2.0° |
| 40 | 0.92 | ±1.0° |
| 60 | 0.95 | ±0.6° |
| 80 | 0.93 | ±0.9° |
| 90 | (Unmeasurable) | (Unmeasurable) |
| 180 | (Unmeasurable) | (Unmeasurable) |

As shown in Table 1, the sugar content was detectable in an accuracy of plus-minus 1.0°Brix (which is a resolving limit of sugar content that can be perceived by humans) or higher (i.e., the error of measurements of sugar content is plus-minus 1.0°Brix or below) when the disposition angle ($\theta$) was set at 40 degrees, 60 degrees or 80 degrees. However, the sugar content of the muskmelons could not be measured in an accuracy of plus-minus 1.0°Brix when the disposition angle ($\theta$) was set at 30 degrees, 90 degrees or 180 degrees. This was because, in the case of a disposition angle ($\theta$) of 30 degrees, the figures in reading the amount of light necessary for detecting the sugar content in an accuracy of plus-minus 1.0°Brix became greater than four figures. In the case of a disposition angles ($\theta$) of 90 degrees or 180 degrees, the coefficient of correlation and the error of measurements of sugar content were unmeasurable because the amount of detection light became 10 nW or lower and muskmelons on which the sugar content itself was unmeasurable were present in the 80 muskmelons.

EXAMPLE 2

Non-destructive measurement of sugar content was made on watermelons, using the same apparatus as in Example 1 except that the muskmelons were replaced with watermelons of about 20 cm diameter.

Figure 7:
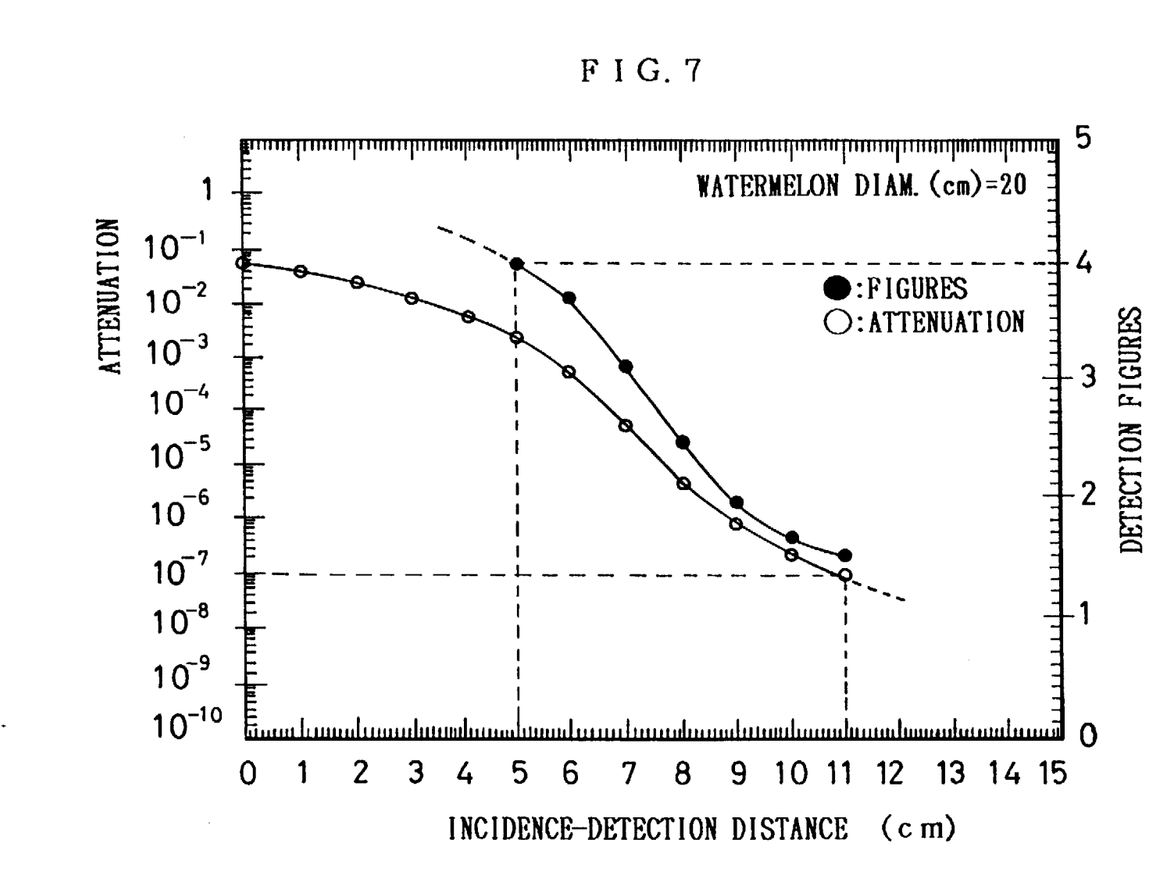
FIG. 7 is a graph showing the dependence of detection figures (figures at which the amount of detection light is read) and attenuation of detection light intensity, on the distance between the center of light-incident area and the center of detection area.

FIG. 7 shows the results of the measurement. More specifically, the linear distance ($\alpha$) corresponding to a line connecting the center of the light-incident area (about 20 mm diameter) formed on the surface of a watermelon by the incident light and the center of the detection area (about 10×10 mm$^2$) formed on the surface of the watermelon by the emergent light (i.e., the distance between the centers of the light-incident and detection areas) are varied to make the measurement. FIG. 7 is a graph showing the dependence on the above linear distance ($\alpha$), of the figures in reading the amount of light necessary for detecting the sugar content in an accuracy of plus-minus 1.0°Brix, and also showing the dependence of attenuation of detection light intensity on the linear distance ($\alpha$).

As is seen from the graph of FIG. 7, in order to measure the sugar content of watermelons of about 20 cm diameter in an accuracy of plus-minus 1.0°Brix or higher, the distance ($\alpha$) between the centers of the light-incident and detection areas must be at least 5 cm (because of the requirement of detector's reading at four figures or less), and the distance at which the attenuation becomes greater than 1×10$^{-7}$, i.e., the distance ($\alpha$) between the centers of the light-incident and detection areas must be 11 cm or less so that the amount or intensity of detection light can be 10 nW or more.

EXAMPLE 3

Figure 8:
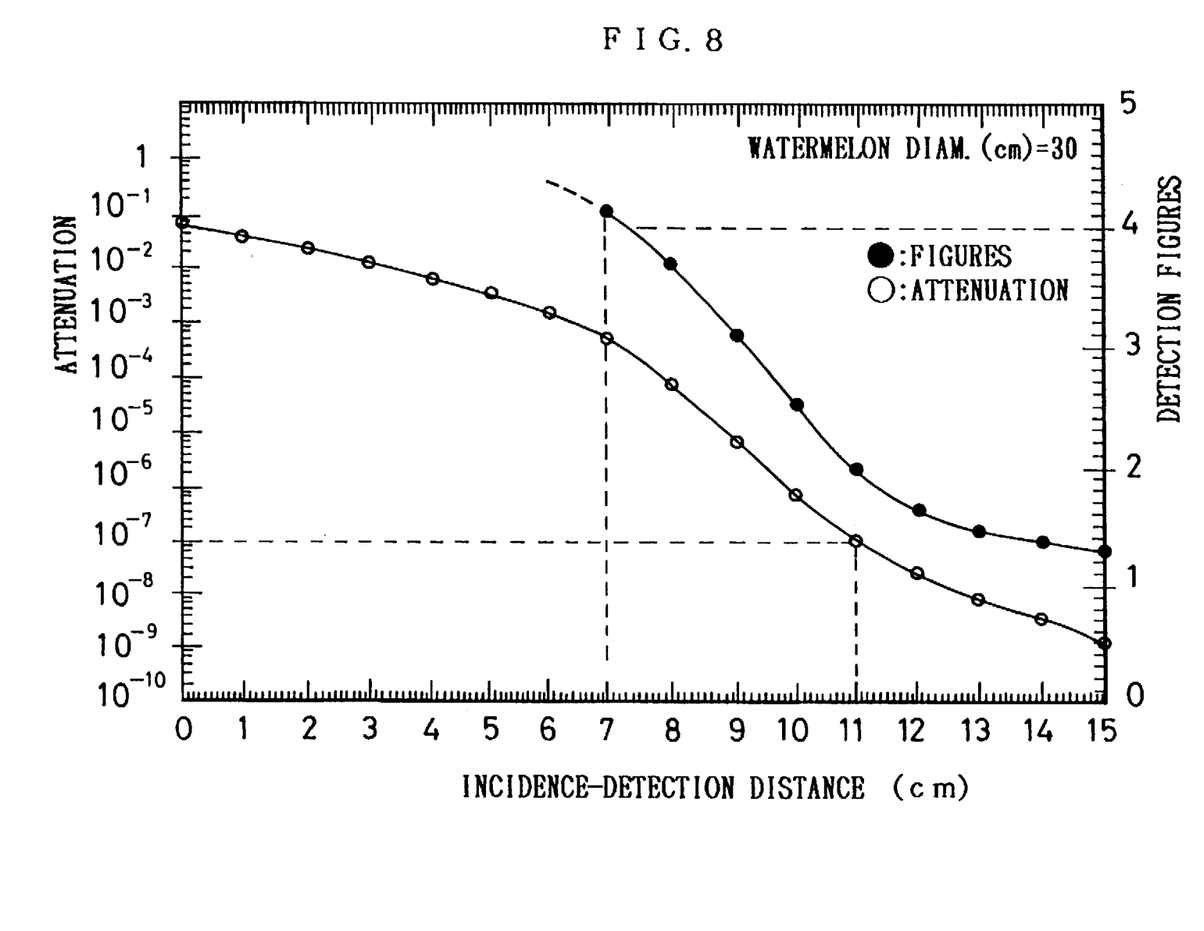
FIG. 8 is another graph showing the dependence of detection figures (figures at which the amount of detection light is read) and attenuation of detection light intensity, on the distance between the center of light-incident area and the center of detection area.

Non-destructive measurement of sugar content was made in the same manner as in Example 2 except that it was made on watermelons of about 30 cm diameter.

FIG. 8 shows the results of the measurement. As is seen from the graph shown therein, in order to measure the sugar content of watermelons of about 30 cm diameter in an accuracy of plus-minus 1.0°Brix or higher, the distance ($\alpha$) between the centers of the light-incident and detection areas must be set within the range of from 7 cm to 11 cm for the same reason as in Example 2.

EXAMPLE 4

Non-destructive measurement of sugar content was made in the same manner as in Example 3 except that the watermelons of about 30 cm diameter were again measured after a week.

Figure 9:
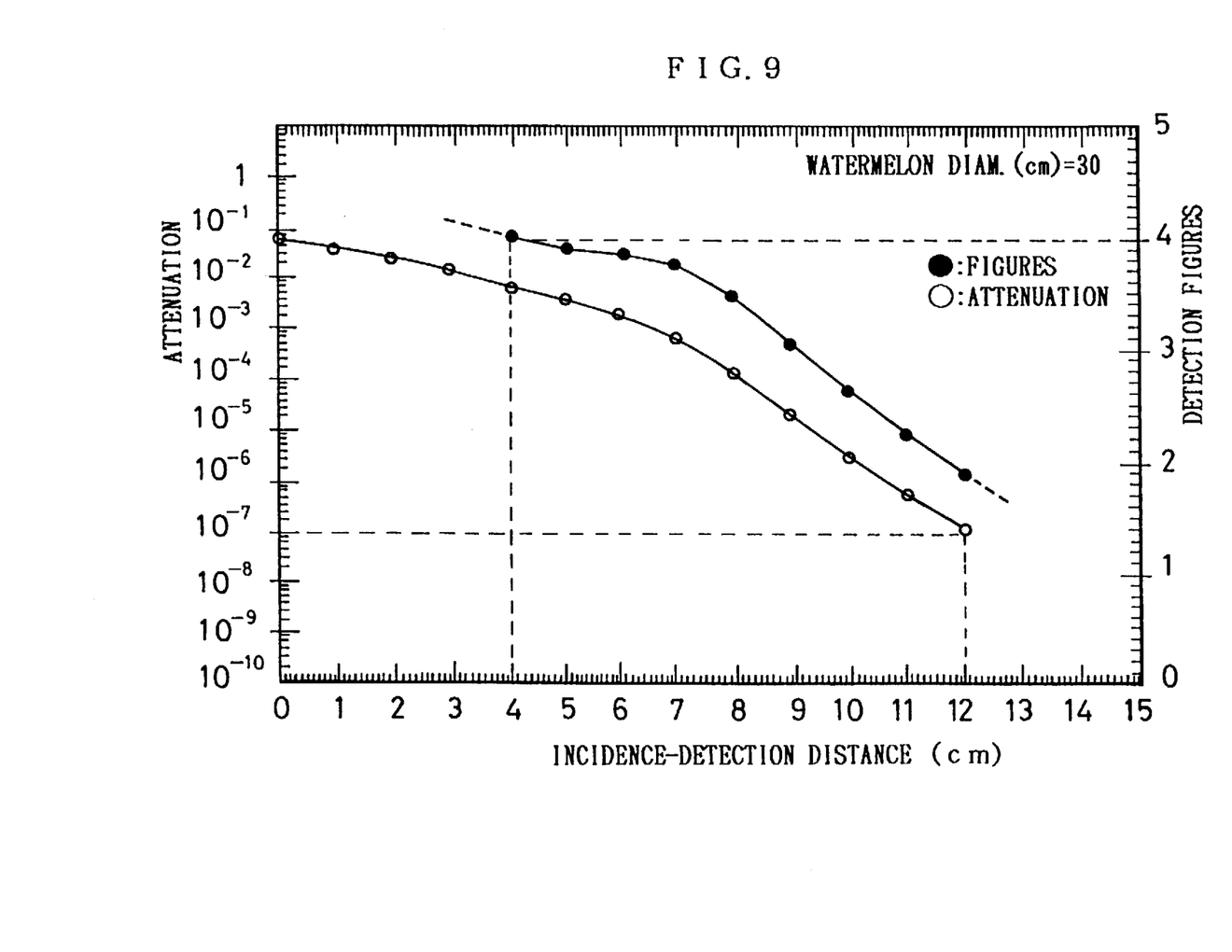
FIG. 9 is still another graph showing the dependence of detection figures (figures at which the amount of detection light is read) and attenuation of detection light intensity, on the distance between the center of light-incident area and the center of detection area.

FIG. 9 shows the results of the measurement. As is seen from the graph shown therein, in order to measure the sugar content of watermelons of about 30 cm diameter, having more ripened, in an accuracy of plus-minus 1.0°Brix or higher, the distance ($\alpha$) between the centers of the light-incident and detection areas must be set within the range of from 4 cm to 12 cm for the same reason as in Example 2.

EXAMPLE 5

In the present Example, a non-destructive sugar content measuring apparatus is used which is substantially the same as the apparatus according to Example 1, shown in FIG. 1, except that different light sources are used. More specifically, as the light sources 1, a laser diode having a laser output of 100 mW and a titanium-sapphire laser having a laser output of 100 mW and also wavelength-variable outputs. The light rays emitted from the laser diode and the titanium-sapphire laser are led through the optical fiber 2 and transmitted to the lens 3. After the light rays are formed into parallel rays of light with a beam diameter of 2 cm, the light is incident on the muskmelon 4. The light incident on the muskmelon 4 is emergent from the muskmelon 4 in every direction on account of the reflection from the surface and the scattering inside the muskmelon 4.

In the present Example, the light emergent from the muskmelon 4 was detected by means of the detector 5 so positioned as to be in a disposition angle ($\theta$) of 60 degrees, as an angle formed by an optical axis of the light incident on the muskmelon 4 toward its center and an optical axis which is perpendicular to the light-receiving face of the detector for detecting the light emergent from the muskmelon 4 and extends toward the center of the muskmelon.

The values of the amount of detection light detected by the detector 5 are converted to digital signals through the 16 bit AD convertor 6 so as to be read in a precision of four figures, and then inputted to the computer 7.

To measure the sugar content, like Example 1, a value of the mount of incident light is beforehand measured and, using this value, a value of the amount of detection light is converted into transmittance (=amount of detection light/ amount of incident light). Thereafter the sugar content is calculated according to the following expression (1).

$$Y=AX_1+BX_2+CX_3+D \tag{1}$$

wherein Y is a sugar content (Brix); $X_1$, $X_2$, $X_3$ are each a natural logarithm value of the transmittance of a muskmelon to the light having wavelengths of 880 nm, 910 nm and 930 nm, i.e., an absorption; and A, B, C and D are each a constant determined by minimum involution with use of actual measurements of sugar content determined by a refraction saccharometer (destructive measurement), where A is –27.39, B is 68.50, C is –41.12 and D is 12.92.

The sugar content was measured under 75 combinations of the wavelengths to determine the correlation with the sugar content determined by the refraction saccharometer. As the present Example, 68 combinations were selected, and as Comparative Example, 7 combinations.

Results obtained are shown in Tables 2 and 3. Table 2 shows the results obtained when the combinations of wavelengths of the present Example are used, and Table 3, the results obtained when the combinations of wavelengths of Comparative Example are used.

TABLE 2

| First light (nm) | Second light (nm) | Third light (nm) | Coefficient of correlation |
| --- | --- | --- | --- |
| 860 | 900 | 921 | 0.95 |
| 880 | 900 | 921 | 0.96 |
| 890 | 900 | 921 | 0.95 |
| 860 | 905 | 921 | 0.95 |
| 880 | 905 | 921 | 0.96 |
| 890 | 905 | 921 | 0.95 |
| 860 | 910 | 921 | 0.95 |
| 880 | 910 | 921 | 0.97 |
| 890 | 910 | 921 | 0.95 |
| 860 | 915 | 921 | 0.95 |
| 880 | 915 | 921 | 0.96 |
| 890 | 915 | 921 | 0.95 |
| 860 | 900 | 925 | 0.95 |

TABLE 2-continued

| First light (nm) | Second light (nm) | Third light (nm) | Coefficient of correlation |
| --- | --- | --- | --- |
| 880 | 900 | 925 | 0.95 |
| 890 | 900 | 925 | 0.95 |
| 860 | 905 | 925 | 0.96 |
| 880 | 905 | 925 | 0.96 |
| 890 | 905 | 925 | 0.95 |
| 860 | 910 | 925 | 0.95 |
| 880 | 910 | 925 | 0.96 |
| 890 | 910 | 925 | 0.95 |
| 860 | 915 | 925 | 0.96 |
| 880 | 915 | 925 | 0.96 |
| 890 | 915 | 925 | 0.95 |
| 860 | 900 | 926 | 0.94 |
| 880 | 900 | 926 | 0.93 |
| 890 | 900 | 926 | 0.93 |
| 860 | 910 | 926 | 0.93 |
| 880 | 910 | 926 | 0.94 |
| 890 | 910 | 926 | 0.94 |
| 860 | 920 | 926 | 0.94 |
| 880 | 920 | 926 | 0.93 |
| 890 | 920 | 926 | 0.92 |
| 860 | 900 | 930 | 0.93 |
| 880 | 900 | 930 | 0.93 |
| 890 | 900 | 930 | 0.93 |
| 860 | 910 | 930 | 0.93 |
| 880 | 910 | 930 | 0.93 |
| 890 | 910 | 930 | 0.92 |
| 860 | 920 | 930 | 0.92 |
| 880 | 920 | 930 | 0.92 |
| 890 | 920 | 930 | 0.92 |
| 860 | 900 | 931 | 0.93 |
| 880 | 900 | 931 | 0.93 |
| 890 | 900 | 931 | 0.92 |
| 860 | 910 | 931 | 0.92 |
| 880 | 910 | 931 | 0.93 |
| 890 | 910 | 931 | 0.93 |
| 860 | 920 | 931 | 0.93 |
| 880 | 920 | 931 | 0.93 |
| 890 | 920 | 931 | 0.92 |
| 860 | 900 | 940 | 0.93 |
| 880 | 900 | 940 | 0.92 |
| 890 | 900 | 940 | 0.92 |
| 860 | 910 | 940 | 0.93 |
| 880 | 910 | 940 | 0.92 |
| 890 | 910 | 940 | 0.92 |
| 860 | 920 | 940 | 0.92 |
| 880 | 920 | 940 | 0.92 |
| 890 | 920 | 940 | 0.92 |
| 880 | 907 | 921 | 0.91 |
| 880 | 907 | 925 | 0.91 |
| 880 | 900 | 950 | 0.90 |
| 880 | 910 | 950 | 0.91 |
| 880 | 920 | 950 | 0.90 |
| 880 | 900 | 960 | 0.90 |
| 880 | 910 | 960 | 0.90 |
| 880 | 920 | 960 | 0.90 |

TABLE 3

| First light (nm) | Second light (nm) | Third light (nm) | Coefficient of correlation |
| --- | --- | --- | --- |
| 850 | 900 | 925 | 0.87 |
| 895 | 900 | 925 | 0.89 |
| 850 | 910 | 925 | 0.88 |
| 895 | 910 | 925 | 0.89 |
| 850 | 910 | 930 | 0.87 |
| 895 | 920 | 930 | 0.88 |
| 895 | 920 | 940 | 0.83 |

As shown in Table 2, when the combinations of wavelengths of the present Example are used, the coefficient of correlation with the actual sugar content is 0.9 or above in all instances. That is, it follows that the sugar content can be measured in an accuracy of plus-minus 1.0°Brix, which is a resolving limit of sugar content that can be perceived by humans.

On the other hand, as shown in Table 3, the coefficient of correlation of 0.9 or above is not obtained, when the combinations of wavelengths of Comparative Example are used.

EXAMPLE 6

Figure 2:
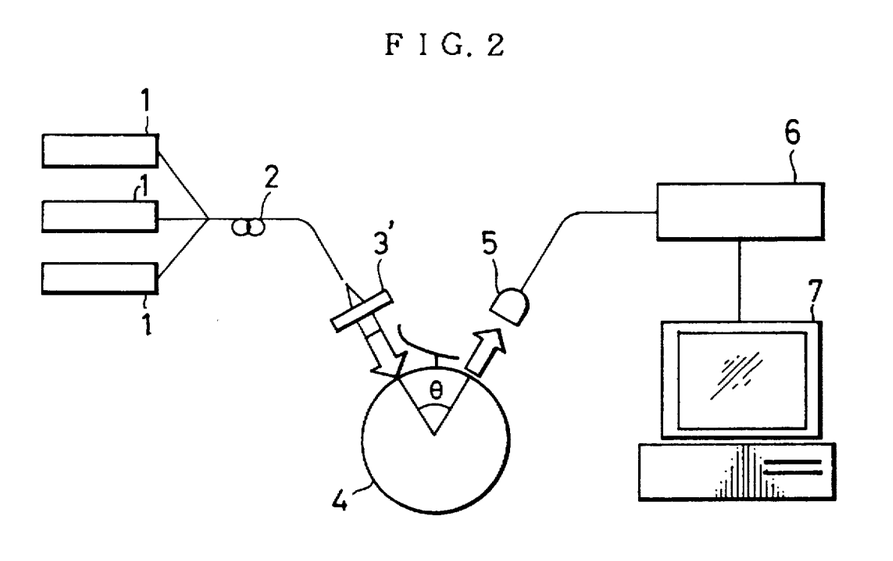
FIG. 2 illustrates the constitution of the non-destructive sugar content measuring apparatus according to another embodiment of the present invention.

In the present Example, a non-destructive sugar content measuring apparatus is used which is substantially the same as the apparatus according to Example 1 except that the lens 3 is replaced with a diffuser panel 3' as shown in FIG. 2.

More specifically, as the light sources 1, three laser diodes are used, each having a laser output of 100 mW and respectively having oscillation wavelengths of 880 nm, 910 nm and 930 nm. The light rays emitted from the laser diodes are led through an optical fiber 2 and transmitted to the diffuser panel 3'. After the light rays are passed through the diffuser panel 3' to make light rays with the respective wavelengths into incident light having equal light intensity distribution, the light is incident on the muskmelon 4 on the surface of which a net is formed. The light incident on the muskmelon 4 is emergent from the muskmelon 4 in every direction on account of the reflection from the surface and the scattering inside the muskmelon 4.

In the present Example, the light emergent from the muskmelon 4 was detected by means of the detector 5 so positioned as to be in a disposition angle (θ) of 60 degrees, as an angle formed by an optical axis of the light incident on the muskmelon 4 toward its center and an optical axis which is perpendicular to the light-receiving face of the detector for detecting the light emergent from the muskmelon 4 and extends toward the center of the muskmelon.

The values of the amount of detection light detected by the detector 5 are converted to digital signals through the 16 bit AD convertor 6 so as to be read in a precision of four figures, and then inputted to the computer 7.

To measure the sugar content, like Example 1, a value of the mount of incident light is beforehand measured and, using this value, a value of the amount of detection light is converted into transmittance (=amount of detection light/ amount of incident light). Thereafter the sugar content is calculated according to the following expression (1).

$$Y = AX_1 + BX_2 + CX_3 + D \qquad (1)$$

wherein Y is a sugar content (Brix); $X_1$, $X_2$, $X_3$ are each a natural logarithm value of the transmittance of a muskmelon to the light having wavelengths of 880 nm, 910 nm and 930 nm, i.e., an absorption; and A, B, C and D are each a constant determined by minimum involution with use of actual measurements of sugar content determined by a refraction saccharometer (destructive measurement), where A is −27.39, B is 68.50, C is −41.12 and D is 12.92.

The size of the diffuser panel 3' was varied so as to form six kinds of incident light having light-incident areas of 0.8 cm², 1.1 cm², 7.1 cm², 12.6 cm², 19.6 cm² and 28.3 cm² respectively The position of the light incidence on the muskmelon 4 was also varied at 8 positions. In this way, the dependence of errors in measurements of sugar content on the light-incident area was observed. The relationship between the light-incident area and the error of measurements of sugar content were as shown in Table 4.

TABLE 4

| Light-incident area (cm²) | Error of measurements of sugar content (Brix) |
|---|---|
| 0.8 | ±2.0 |
| 1.1 | ±1.0 |
| 7.1 | ±0.6 |
| 12.6 | ±0.9 |
| 19.6 | ±1.0 |
| 28.3 | ±1.5 |

As is seen from Table 4, the sugar content can be measured in an accuracy of about plus-minus 1.0°Brix, which is a resolving limit of sugar content that can be perceived by humans, when the light-incident areas is 1.1 cm², 7.1 cm², 12.6 cm² or 19.6 cm² even if the light-incident position is varied. On the other hand, the sugar content can not be measured in an accuracy of plus-minus 1.0°Brix when the light-incident area is 0.8 cm² or 28.3 cm².

For comparison, the sugar content was measured in the manner that light-incident area on the surface of the muskmelon, of the light emitted from the three light sources, was fixed to 7.1 cm² and the respective light-incident positions were successively shifted by 2 mm on the surface of the muskmelon. As a result, the light intensity distribution became non-uniform, and the error of measurements of sugar content was plus-minus 1.2°Brix, not satisfying the accuracy of plus-minus 1.0°Brix.

EXAMPLE 7

In the present Example, a non-destructive sugar content measuring apparatus is used which is substantially the same as the apparatus according to Example 1 except that as shown in FIG. 2 an optical fiber that emits laser light, a muskmelon 4 and a detector 5 that detects the light emergent from the muskmelon 4 are placed in a darkroom and that the light-incident position of the laser light on the muskmelon 4 and the position where the emergent light is detected are provided at a lower side of the muskmelon 4. The optical fiber 2 and the lens 3, and the detector 5 are respectively held in tube members 8. Also, a ring-shaped rubber 9 is fitted to the end of each tube member 8.

Into the dark room, 50 muskmelons, their sugar content being unknown, were transported and the sugar content (Dn) of each muskmelon was measured in the same manner as in Example 1. Here, as shown in FIG. 3, the laser light was made incident and the emergent laser light was detected both at such positions that the height (h) of the fruit as viewed with its pedicel portion up was at $1/15$ of the overall height (H) and that the light-incident direction and detection direction of the laser light were in the directions toward the center of the muskmelon and these directions were included in the same plane and also not on the same longitude (i.e., the position of light incidence and the position of detection do not overlap).

Next, fruit juice was collected from each muskmelon to determine its sugar content (D'n) by means of a saccharometer utilizing refractive indexes to further determine values of (Dn/D'n). As the result, the values of (Dn/D'n) were all within the range of from 1.05 to 0.9.

EXAMPLE 8

An experiment was made in the same manner as in Example 7 except that the laser light was made incident at such a position that the height (h) of the fruit as viewed with its pedicel portion up was at $1/15$ of the overall height (H), the emergent laser light was detected at such a position that the height (h) of the fruit as viewed with its pedicel portion up was at $14/15$ of the overall height (H) and on the same longitude as the light-incident position of the laser light, and the light-incident direction and detection direction of the laser light were in the directions toward the center of the muskmelon and these directions were included in the same plane. As the result, the values of (Dn/D'n) were all within the range of the 1.05 to 0.95.

EXAMPLE 9

An experiment was made in the manner as in Example 7 except that the laser light was made incident at such a position that the height (h) of the fruit as viewed with its pedicel portion up was at $14/15$ of the overall height (H), the emergent laser light was detected at such a position that the height (h) of the fruit as viewed with its pedicel portion up was at $1/15$ of the overall height (H) and on the same longitude as the light-incident position of the laser light, and the light-incident direction and detection direction of the laser light were in the directions toward the center of the muskmelon and these directions were included in the same plane. As the result, the values of (Dn/D'n) were all within the range of from 1.05 to 0.95.

EXAMPLE 10

An experiment was made in the same manner as in Example 7 except that the laser light was made incident and the emergent laser light was detected both at such positions that the height (h) of the fruit as viewed with its pedicel portion up was at $3/10$ of the overall height (H), and the light-incident direction and detection direction of the laser light were in the directions toward the center of the muskmelon and these directions were included in the same plane and also not on the same longitude. As the result, the values of (Dn/D'n) were all within the range of from 1.05 to 0.95.

EXAMPLE 11

An experiment was made in the same manner as in Example 7 except that the laser light was made incident and the emergent laser light was detected both at such positions that the height (h) of the fruit as viewed with its pedicel portion up was at $1/3$ of the overall height (H), and the light-incident direction and detection direction of the laser light were in the directions toward the center of the muskmelon and these directions were included in the same plane and also not on the same longitude. As the result, the values of (Dn/D'n) were all within the range of from 1.05 to 0.95.

Comparative Example 1

An experiment was made in the same manner as in Example 7 except that the laser light was made incident and the emergent laser light was detected both at such positions that the height (h) of the fruit as viewed with its pedicel portion up was at $1/2$ of the overall height (H), and the light-incident direction and detection direction of the laser light were in the directions toward the center of the muskmelon and these directions were directly opposite to each other. As the result, the values of (Dn/D'n) were within the range of from 1.05 to 0.95 in respect of 38 muskmelons, and in the range of from 1.10 to 1.05 or 0.95 to 0.90 in respect of 12 muskmelons.

Comparative Example 2

An experiment was made in the same manner as in Example 7 except that the laser light was made incident and the emergent laser light was detected both at such positions that the height (h) of the fruit as viewed with its pedicel portion up was at 7/10 of the overall height (H), and the light-incident direction and detection direction of the laser light were in the directions toward the center of the muskmelon and these directions were included in the same plane and also not on the same longitude. As the result, the values of (Dn/D'n) were within the range of from 1.05 to 0.95 in respect of 34 muskmelons, and in the range of from 1.10 to 1.05 or 0.95 to 0.90 in respect of 16 muskmelons.

What is claimed is:

1. A non-destructive sugar content measuring apparatus for determining the sugar content of a vegetable or fruit by measuring absorption of light in sugar when near infrared light is made incident on the vegetable or fruit; said apparatus comprising:

at least one light source that emits a first light ray having a wavelength ranging between 860 nm and 890 nm, a second light ray having a wavelength ranging between 900 nm and 920 nm and a third light ray having a wavelength ranging between more than 920 nm and not more than 960 nm, and a detector that detects the absorption of light; said detector being disposed at a position except the position on an extended line of a straight line that connects i) the center of a light-incident area formed on the surface of the vegetable or fruit by the light emitted from the light source and incident on the vegetable or fruit, and (ii) the center of the vegetable or fruit, and at the same time at a position where the light-incident area formed on the surface of the vegetable or fruit by the incident light and a detection area formed on the surface of the vegetable or fruit by the light emergent from the vegetable or fruit and to be received by the detector do not overlap each other.

2. The non-destructive sugar content measuring apparatus according to claim 1, wherein said vegetable or fruit is a muskmelon, and an angle formed by i) a straight line that connects the center of a light-incident area formed on the surface of the muskmelon by the light incident thereon and the center of the muskmelon and ii) a straight line that connects the center of a detection area formed on the surface of the muskmelon by the light emergent therefrom and the center of the muskmelon is set at from 40 degrees to 80 degrees.

3. The non-destructive sugar content measuring apparatus according to claim 1, wherein said vegetable or fruit is a muskmelon, and the linear distance corresponding to a straight line connecting the center of the light-incident area formed on the surface of the muskmelon by the incident light and the center of a detection area formed on the surface of the muskmelon by the emergent light is set at from 4 cm to 13 cm.

4. The non-destructive sugar content measuring apparatus according to claim 1, wherein said vegetable or fruit is a watermelon, and the linear distance corresponding to a straight line connecting the center of the light-incident area formed on the surface of the watermelon by the incident light and the center of a detection area formed on the surface of the watermelon by the emergent light is set at from 4 cm to 12 cm.

5. The non-destructive sugar content measuring apparatus according to claim 1, wherein the incident direction of the light emitted from the light source and incident on the surface of the vegetable or fruit is set in the direction not in agreement with the direction extended from a straight line connecting the center of the light-incident area formed on the surface of the vegetable or fruit by the incident light and the center of the vegetable or fruit.

6. The non-destructive sugar content measuring apparatus according to claim 1, wherein said light source is a semiconductor laser.

7. The non-destructive sugar content measuring apparatus according to claim 1, wherein said light source is a solid-state laser.

8. The non-destructive sugar content measuring apparatus according to claim 1, wherein said light source is a light-emitting diode.

9. The non-destructive sugar content measuring apparatus according to claim 1, wherein said second light ray has a wavelength ranging between 900 and 905 nm or between 910 nm and 915 nm, and said third light ray has a wavelength ranging between more than 920 nm and not more than 925 nm.

10. The non-destructive sugar content measuring apparatus according to claim 1, wherein said second light ray has a wavelength ranging between more than 905 nm and not more than 910 nm, and said third light ray has a wave length ranging between more than 920 nm and not more than 925 nm.

11. The non-destructive sugar content measuring apparatus according to claim 1, wherein said third light ray has a wavelength ranging between more than 925 nm and not more than 930 nm.

12. The non-destructive sugar content measuring apparatus according to claim 1, wherein said third light ray has a wavelength ranging between more than 930 nm and not more than 940 nm.

13. The non-destructive sugar content measuring apparatus according to any one of claims 1 to 8, wherein said vegetable or fruit is a muskmelon, said first to third light rays emitted from at least one light source and incident on the muskmelon have equal extent of the light-incident area and equal light intensity distribution in the light-incident area on the surface of the muskmelon, and the extent of light-incident area is set within the range of from 1 cm$^2$ to 20 cm$^2$.

14. The non-destructive sugar content measuring apparatus according to claim 13, wherein said first to third light rays emitted from at least one light source and incident on the muskmelon are passed through a diffuser panel so that the incident light rays have equal light intensity distribution in the light-incident area on the surface of the muskmelon.

15. The non-destructive sugar content measuring apparatus according to any one of claims 1 to 8, wherein said vegetable or fruit is a fruit, and the light-incident area formed on the surface of the fruit by the incident light and/or the detection area formed on the surface of the fruit by the light emergent from the fruit and to be received by the detector is set at a position within the range of from 1/50 to 1/3 of the overall height of the fruit as viewed with its pedicel portion up.

* * * * *